United States Patent [19]

Junggren et al.

[11] 4,337,257
[45] Jun. 29, 1982

[54] GASTRIC ACID SECRETION INHIBITING SUBSTITUTED 2-(2-BENZIMIDAZOLYL)-PYRIDINES, THEIR PREPARATION, PHARMACEUTICAL PREPARATIONS CONTAINING SAME, AND METHOD FOR INHIBITING GASTRIC ACID SECRETION

[75] Inventors: Ulf K. Junggren, Mölnlycke; Sven E. Sjöstrand, Kungsbacka, both of Sweden

[73] Assignee: Aktiebolaget Hässle, Mölndal, Sweden

[21] Appl. No.: 150,965

[22] Filed: May 19, 1980

Related U.S. Application Data

[62] Division of Ser. No. 27,277, Apr. 5, 1979, Pat. No. 4,255,431.

[30] Foreign Application Priority Data

Apr. 14, 1978 [SE] Sweden ............................... 7804231

[51] Int. Cl.³ ..................... A61K 31/44; C07D 401/12
[52] U.S. Cl. .................................... 424/263; 546/271
[58] Field of Search ........................ 546/271; 424/263

[56] References Cited

U.S. PATENT DOCUMENTS 4,045,563 8/1977 Berntsson et al. ............. 546/271 X
4,045,564 8/1977 Berntsson et al. ............. 546/271 X

OTHER PUBLICATIONS

Berglindh, T., et al. *Acta Physiol. Scand.* 1976, 96, 150–159.
Berglindh, T., et al. *Acta Physiol. Scand.* 1976, 97, 401–414.

*Primary Examiner*—Richard A. Schwartz
*Attorney, Agent, or Firm*—Brumbaugh, Graves, Donohue & Raymond

[57] ABSTRACT

The present invention relates to novel compounds of the formula

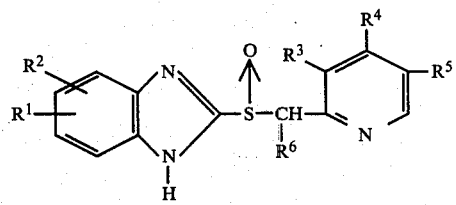

wherein $R^1$ and $R^2$ are the same or different and are each hydrogen, alkyl, halogen, carbomethoxy, carbethoxy, alkoxy, or alkanoyl, $R^6$ is hydrogen, methyl or ethyl, $R^3$, $R^4$ and $R^5$ are the same or different and are each hydrogen, methyl, methoxy, ethoxy, methoxyethoxy or ethoxyethoxy whereby $R^3$, $R^4$ and $R^5$ are not all hydrogen, and whereby when two of $R^3$, $R^4$ and $R^5$ are hydrogen the third of $R^3$, $R^4$ and $R^5$ is not methyl. The compounds are potent gastric acid secretion inhibitors.

23 Claims, No Drawings

GASTRIC ACID SECRETION INHIBITING SUBSTITUTED 2-(2-BENZIMIDAZOLYL)-PYRIDINES, THEIR PREPARATION, PHARMACEUTICAL PREPARATIONS CONTAINING SAME, AND METHOD FOR INHIBITING GASTRIC ACID SECRETION

This is a division, of application Ser. No. 027,277, filed Apr. 5, 1979, now U.S. Pat. No. 4,255,431.

The present invention relates to new compounds having valuable properties in affecting gastric acid secretion in mammals, including man, as well as the process for their preparation, method of affecting gastric acid secretion and pharmaceutical preparations containing said novel compounds.

The object of the present invention is to obtain compounds which affect gastric acid secretion, and which inhibit exogenously or endogenously stimulated gastric acid secretion. These compounds can be used in the treatment of peptic ulcer disease.

It is previously known that compounds of the formulas I and II

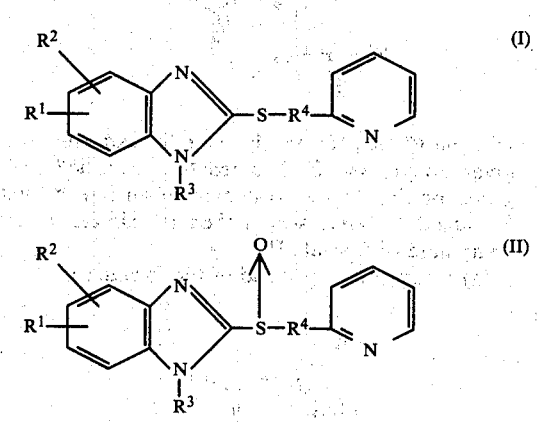

wherein $R^1$ and $R^2$ are each selected from the group consisting of hydrogen, alkyl, halogen, cyano, carboxy, carboxyalkyl, carboalkoxy, carboalkoxyalkyl, carbamoyl, carbamoyloxy, hydroxy, alkoxy, hydroxyalkyl, trifluoromethyl and acyl in any position, $R^3$ is selected from the group consisting of hydrogen, alkyl, acyl, carboalkoxy, carbamoyl, alkylcarbamoyl, dialkylcarbamoyl, alkylcarbonylmethyl, alkoxycarbonylmethyl, and alkylsulphonyl, and $R^4$ is selected from the group consisting of straight and branched alkylene groups having 1 to 4 carbon atoms, whereby at most one methylene group is present between S and the pyridyl group, and whereby the pyridyl group may be further substituted with alkyl or halogen, possess an inhibiting effect on gastric acid secretion.

It has now, however, surprisingly been found that the compounds defined below possess a still greater inhibiting effect than those given above.

Compounds of the invention are those of the general formula III

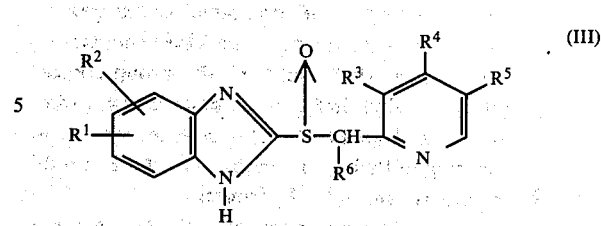

wherein $R^1$ and $R^2$ are same or different and are each selected from the group consisting of hydrogen, alkyl, halogen, carbomethoxy, carbethoxy, alkoxy, and alkanoyl, $R^6$ is selected from the group consisting of hydrogen, methyl, and ethyl, and $R^3$, and $R^5$ are the same or different and are each selected from the group consisting of hydrogen, methyl, methoxy, ethoxy, methoxyethoxy and ethoxyethoxy and $R^4$ is hydrogen or methyl whereby $R^3$, $R^4$, and $R^5$ are not all hydrogen, and whereby when two of $R^3$, $R^4$, and $R^5$ are hydrogen, the third of $R^3$, $R^4$ and $R^5$ is not methyl.

Alkyl $R^1$ and $R^2$ of formula III are suitably alkyl having up to 7 carbon atoms, preferably up to 4 carbon atoms. Thus, alkyl R may be methyl, ethyl, n-propyl, isopropyl, n-butyl or isobutyl.

Halogen $R^1$ and $R^2$ are chloro, bromo, fluoro, or iodo.

Alkoxy $R^1$ and $R^2$ are suitably alkoxy groups having up to 5 carbon atoms, preferably up to 3 carbon atoms, such as methoxy, ethoxy, n-propoxy, or isopropoxy.

Alkanoyl $R^1$ and $R^2$ have preferably up to 4 carbon atoms and are e.g. formyl, acetyl, or propionyl, preferably acetyl.

A preferred group of compounds of the general formula III are those wherein $R^1$ and $R^2$ are the same or different and are each selected from the group consisting of hydrogen, alkyl, carbomethoxy, alkoxy, and alkanoyl, whereby $R^1$ and $R^2$ are not both hydrogen, $R^6$ is hydrogen, and $R^3$, $R^4$, and $R^5$ are the same or different and are each selected from the group consisting of hydrogen, methyl, methoxy, and ethoxy, whereby $R^3$, $R^4$, and $R^5$ are not all hydrogen, and whereby when two of $R^3$, $R^4$, and $R^5$ are hydrogen the third of $R^3$, $R^4$, and $R^5$ is not methyl.

A second preferred group of compounds of the general formula III are those wherein $R^1$ and $R^2$ are the same or different and are each selected from the group consisting of hydrogen, alkyl, halogen, carbomethoxy, carbethoxy, alkoxy, and alkanoyl, $R^6$ is selected from the group consisting of hydrogen, methyl, and ethyl, $R^3$ is methyl, $R^4$ is methoxy, and $R^5$ is methyl.

A third preferred group of compounds of the general formula III are those wherein $R^1$ and $R^2$ are the same or different and are each selected from the group consisting of hydrogen, alkyl, halogen, carbomethoxy, carbethoxy, alkoxy and alkanoyl, $R^6$ is selected from the group consisting of hydrogen, methyl and ethyl, and $R^3$ is hydrogen, $R^4$ is methoxy and $R^5$ is methyl or $R^3$ is methyl, $R^4$ is methoxy and $R^5$ is hydrogen.

A fourth preferred group of compounds of the general formula III are those wherein $R^1$ and $R^2$ are the same or different and are each selected from the group consisting of hydrogen, alkyl, halogen, carbomethoxy, carbethoxy, alkoxy, and alkanoyl, $R^6$ is selected from the group consisting of hydrogen, methyl and ethyl, $R^3$ and $R^5$ are hydrogen and $R^4$ is methoxy.

A fifth preferred group of compounds of the general formula III are those wherein $R^1$ and $R^2$ are the same or different and are each selected from the group consisting of hydrogen, alkyl, halogen, carbomethoxy, carbethoxy, alkoxy, and alkanoyl, $R^6$ is selected from the group consisting of hydrogen, methyl and ethyl, and $R^3$ and $R^5$ are methyl and $R^4$ is hydrogen.

A sixth preferred group of compounds of the general formula III are those wherein $R^1$ and $R^2$ are the same or different and are each selected from the group consisting of hydrogen, alkyl, halogen, carbomethoxy, carbethoxy, alkoxy, and alkanoyl, $R^6$ is selected from the group consisting of hydrogen, methyl and ethyl, $R^3$ and $R^5$ are hydrogen and $R^4$ is ethoxy, methoxyethoxy or ethoxyethoxy.

A seventh preferred group of compounds of the general formula III are those wherein $R^1$ and $R^2$ are the same or different and are each selected from the group consisting of hydrogen, alkyl, halogen, carbomethoxy, alkoxy, and alkanoyl, $R^6$ is selected from the group consisting of hydrogen, methyl, and ethyl, $R^3$, $R^4$, and $R^5$ are all methyl. Other groups of compounds which may be used are:

Compounds in which $R^1$ is hydrogen, chloro, methyl, ethyl, methoxy, acetyl, carboethoxy or carbomethoxy; $R^2$ is hydrogen or methyl; $R^6$ is hydrogen, methyl or ethyl; $R^3$ and $R^5$ are methyl; and $R^4$ is methoxy.

Compounds in which $R^1$ is hydrogen, chloro, methyl, ethyl, methoxy, acetyl, carboethoxy or carbomethoxy; $R^2$ is hydrogen, methyl or ethyl; $R^4$ is methoxy; and $R^3$ is methyl and $R^5$ is hydrogen or $R^3$ is hydrogen and $R^5$ is methyl.

Compounds of formula III above may be prepared according to the following methods:

(a) oxidizing a compound of formula IV

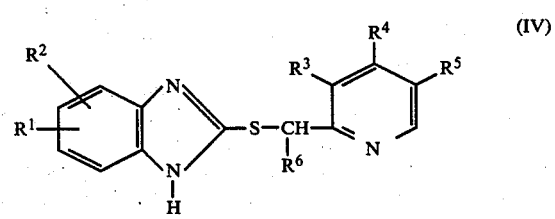

wherein $R^1$, $R^2$, $R^6$, $R^3$, $R^4$, and $R^5$ have the meanings given, to the formation of a compound of formula III.

(b) reacting a compound of the formula V

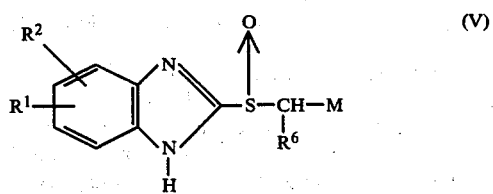

wherein $R^1$, $R^2$, and $R^6$ have the meanings given above and M is a metal selected from the group consisting of K, Na and Li, with a compound of formula VI.

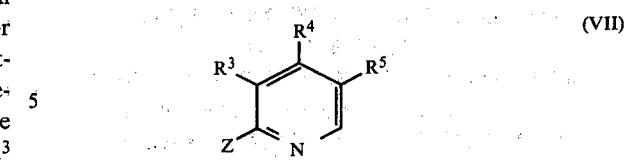

wherein $R^3$, $R^4$, and $R^5$ have the same meanings as given above, Z is a reactive esterified hydroxy group, to the formation of a compound of formula III;

(c) reacting a compound of the formula VII

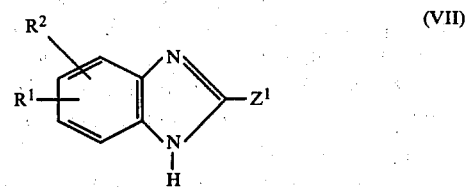

wherein $R^1$, and $R^2$ have the same meanings as given above and $Z^1$ is SH or a reactive esterified hydroxy group, with a compound of the formula VIII

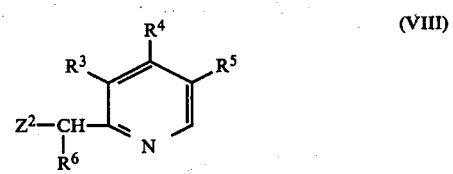

wherein $R^6$, $R^3$, $R^4$, and $R^5$ have the same meanings as given above, and $Z^2$ is a reactive esterified hydroxy group or SH, to the formation of an intermediate of formula IV above, which then is oxidized to give a compound of formula III;

(d) reacting a compound of the formula IX

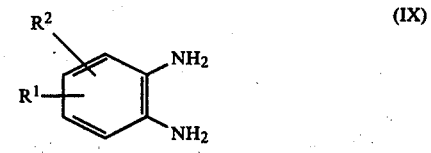

wherein $R^1$ and $R^2$ have the same meanings as given above with a compound of the formula X wherein $R^6$, $R^3$, $R^4$, and $R^5$ have the same meanings as given above, to the formation of an intermediate of formula IV above, which then is oxidized to give a compound of formula III, which compound may be converted to its therapeutically acceptable salts, if so desired.

In the reactions above, Z, $Z^1$, and $Z^2$ may be a reactive, esterified hydroxy group which is a hydroxy group esterified with strong, inorganic or organic acid, preferably a hydrohalogen acid, such as hydrochloric acid, hydrobromic acid, or hydroiodic acid, also sulfuric acid or a strong organic sulfonic acid as a strong aromatic acid, e.g. benzenesulfonic acid, 4-bromobenzenesulfonic acid or 4-toluenesulfonic acid.

The oxidation of the sulfur atom in the chains above to sulfinyl (S→O) takes place in the presence of an oxidizing agent selected from the group consisting of nitric acid, hydrogen peroxide, peracids, peresters, ozone, dinitrogentetraoxide, iodosobenzene, N-halosucinimide, 1-chlorobenzotriazole, t-butylhypochlorite, diazobicyclo-[2,2,2]-octane bromine complex, sodium metaperiodate, selenium dioxide, manganese dioxide, chromic acid, cericammonium nitrate, bromine, chlorine, and sulfuryl chloride. The oxidation usually takes place in a solvent wherein the oxidizing agent is present in some excess in relation to the product to be oxidized.

Depending on the process conditions and the starting materials, the end product is obtained either as the free base or in the acid addition salt, both of which are included within the scope of the invention. Thus, basic, neutral or or mixed salts may be obtained as well as hemi, mono, sesqui or polyhydrates. The acid addition salts of the new compounds may in a manner known per se be transformed into free base using basic agents such as alkali or by ion exchange. On the other hand, the free bases obtained may form salts with organic or inorganic acids. In the prepartion of acid addition salts preferably such acids are used which form suitable therapeutically acceptable salts. Such acids include hydrohalogen acids, sulfonic, phosphoric, nitric, and perchloric acids; aliphatic, alicyclic, aromatic, heterocyclic carboxy or sulfonic acids, such as formic, acetic, propionic, succinic, glycolic, lactic, malic, tartaric, citric, ascorbic, maleic, hydroxymaleic, pyruvic, phenylacetic, benzoic, p-aminobenzoic, antranilic, p-hydroxybenzoic, salicylic or p-aminosalicylic acid, embonic, methanesulfonic, ethanesulfonic, hydroxyethanesulfonic, ethylenesulfonic, halogenbenzenesulfonic, toluenesulfonic, napht-hylsulfonic or sulfanilic acids; methionine, tryptophane, lysine or arginine.

These or other salts of the new compounds, as e.g. picrates, may serve as purifying agents of the free bases obtained. Salts of the bases may be formed, separated from solution, and then the free base can be recovered from a new salt solution in a purer state. Because of the relationship between the new compounds in free base form and their salts, it will be understood that the corresponding salts are included within the scope of the invention.

Some of the new compounds may, depending on the choice of starting mterials and process, be present as optical isomers or racemate, or if they contain at least two asymmetric carbon atoms, be present as an isomer mixture (racemate mixture).

The isomer mixtures (racemate mixtures) obtained may be separated into two stereoisomeric (diastereomeric) pure racemates by means of chromatography or fractional crystallization.

The racemates obtained can be separated according to known methods, e.g. recrystallization from an optically active solvent, use of microorganisms, reactions with optically active acids forming salts which can be separated, separation based on different solubilities of the diastereomers. Suitable optically active acids are the L- and D-forms of tartaric acid, di-o-tolyl-tartaric acid, malic acid, mandelic acid, camphorsulfonic acid or quinic acid, Preferably the more active part of the two antipodes is isolated.

The starting materials are known or may, if they should be new, be obtained according to processes known per se.

In clinical use the compounds of the invention are administered orally, rectally or by injection in the form of a pharmaceutical preparation which contains an active component either as a free base or as a pharmaceutically acceptable, non-toxic acid addition salt, such as hydrochloride, lactate, acetate, sulfamate, in combination with a pharmaceutically acceptable carrier. The carrier may be in the form of a solid, semisolid or liquid diluent, or a capsule. These pharmaceutical preparations are a further object of the invention. Usually the amount of active compound is between 0.1 to 95% by weight of the preparation, between 0.5 to 20% by weight in preparations for injection and between 2 and 50% by weight in preparations for oral administration.

In the preparation of pharmaceutical preparations containing a compound of the present invention in the form of dosage units for oral administration the compound selected may be mixed with a solid, pulverulent carrier, such as lactose, saccharose, sorbitol, mannitol, starch, amylopectin, cellulose derivatives or gelatin, as well as with an antifriction agent such as magnesium stearate, calcium stearate, and polyethyleneglycol waxes. The mixture is then pressed into tablets. If coated tablets are desired, the above prepared core may be coated with a concentrated solution of sugar, which may contain gum arabic, gelatin, talc, titanium dioxide or with a lacquer dissolved in volatile organic solvent or mixture of solvents. To this coating various dyes may be added in order to distinguish among tablets with different active compounds or with different amounts of the active compound present.

Soft gelatin capsules may be prepared which capsules contain a mixture of the active compound or compounds of the invention and vegetable oil. Hard gelatin capsules may contain granules of the active compound in combination with a solid, pulverulent carrier as lactose, saccharose, sorbitol, mannitol, potato starch, corn starch, amylopectin, cellulose derivatives or gelatin.

Dosage units for rectal administration may be prepared in the form of suppositories which contain the active substance in a mixture with a neutral fat base, or they may be prepared in the form of gelatin-rectal capsules which contain the active substance in a mixture with a vegetable oil or paraffin oil.

Liquid preparations for oral administration may be prepared in the form of syrups or suspensions, e.g. solutions containing from 0.2% to 20% by weight of the active ingredient and the remainder consisting of sugar and a mixture of ethanol, water, glycerol and propylene glycol. If desired, such liquid preparations may contain colouring agents, flavouring agents, saccharin and carboxymethylcellulose as a thickening agent.

Solutions for parenteral administration by injection may be prepared as an aqueous solution of a watersoluble pharmaceutically acceptable salt of the active compound, preferably in a concentration from 0.5% to 10% by weight. These solutions may also contain stabilizing agents and/or buffering agents and may be manufactured in different dosage unit ampoules.

Pharmaceutical tablets for oral use are prepared in the following manner: The solid substances are ground or sieved to a certain particle size, and the binding agent is homogenized and suspended in a suitable solvent. The therapeutically active compounds and auxiliary agents are mixed with the binding agent solution. The resulting mixture is moistened to form a uniform suspension having the consistency of wet snow. The moistening causes the particles to aggregate slightly, and the resulting mass is pressed through a stainless steel sieve having a mesh size of approximately 1 mm. The layers of the mixture are dried in carefully controlled drying cabinets for approximately ten hours to obtain the desired particle size and consistency. The granules of the dried mixture are sieved to remove any powder. To this mixture, disintegrating, antifraction and antiadhesive agents are added. Finally, the mixture is pressed into tablets using a machine with the appropriate punches and dies to obtain the desired tablet size. The pressure applied affects the size of the tablet, its strength and its ability to dissolve in water. The compression pressure used should be in the range 0.5 to 5 tons. Tablets are manufactured at the rate of 20.000 to 200.000 per hour. The tablets, especially those which are rough or bitter, may be coated with a layer of sugar or some other palatable substance. They are then packaged by machines having electronic counting devices. The different types of packages consist of glass or plastic gallipots, boxes tubes and specific dosage adapted packages.

The typical daily dose of the active substance varies according to the individual needs and the manner of administration. In general, oral dosages range from 100 to 400 mg/day of active substance and intravenous dosages range from 5 to 20 mg/day. The following illustrates a preferred embodiment of the invention without being limited thereto. Temperature is given in degrees Centigrade.

The starting materials in the examples found below were prepared in accordance with the following methods: (1) a 1,2-diamino compound, such as o-phenylenediamine was reacted with potassium ethylxanthate (according to Org. Synth. Vol. 30, p. 56) to form a 2-mercaptobenzimidazole; (2) the compound 2-chloromethylpyridine was prepared by reacting 2-hydroxymethylpyridine with thionylchloride (according to Arch. Pharm. Vol. 26, pp. 448-451 (1956)); (3) the compound 2-chloromethylbenzimidazole was prepared by condensing o-phenylenediamine with chloroacetic acid.

EXAMPLE 1

28.9 g of 2-[2-(4,5-dimethyl)pyridylmethylthio]-(5-acetyl-6-methyl)-benzimidazole were dissolved in 160 ml of $CHCl_3$, 24.4 g of m-chloroperbenzoic acid were added in portions while stirring and cooling to 5° C. After 10 minutes, the precipitated m-chlorobenzoic acid was filtered off. The filtrate was diluted with $CH_2Cl_2$, washed with $Na_2CO_3$ solution, dried over $Na_2SO_4$ and evaporated in vacuo. The residue crystallized when diluted with $CH_3CN$, and 2-[2-(4,5-dimethyl)pyridylmethylsulfinyl]-(5-acetyl-6-methyl)benzimidazole was recrystallized from $CH_3CN$. Yield 22.3 g; m.p. 158° C.

EXAMPLES 2-30

The preparation of compounds of formula III labelled 2-26 was carried out in accordance with Example 1 above. The compounds prepared are listed in Table 1 which identifies the substituents for these compounds.

EXAMPLE 31 (METHOD C)

0.1 moles of 4-6-dimethyl-2-mercaptobenzimidazole were dissolved in 20 ml of water and 200 ml of ethanol containing 0.2 moles of sodium hydroxide. 0.1 moles of 2-chloromethyl-(3,5-dimethyl)pyridine hydrochloride were added and the mixture was refluxed for two hours. The sodium chloride formed was filtered off and the solution was evaporated in vacuo. The residue was dissolved in acetone and was treated with active carbon. An equivalent amount of concentrated hydrochloric acid was added, whereupon the mono-hydrochloride of 2-[2-(3,5-dimethyl)pyridylmethylthio]-(4,6-dimethyl)benzimidazole was isolated. Yield 0.05 moles.

This compound was then oxidized in accordance with Example 1 above to give the corresponding sulfinyl compound melting point 50°-55° C.

EXAMPLE 32 (METHOD B)

0.1 moles of 2-[Li-methylsulfinyl](5-acetyl-6-methyl)-benzimidazole were dissolved in 150 mls of benzene. 0.1 moles 2-chloro-(3,5-dimethyl)pyridine were added and the mixture was refluxed for two hours. The lithiumchloride formed was filtered off, and the solution was evaporated in vacuo. The residue was crystallized from $CH_3CN$, and recrystallized from the same solvent. Yield 0.82 moles of 2-[2-(3,5-dimethyl)pyridylmethylsulfinyl]-(5-acetyl-6-methyl)benzimidazole melting at 171° C.

EXAMPLE 33 (METHOD D)

23.4 g of 2-[2-(3,4,5-trimethyl)pyridylmethylthio] formic acid and 16.6 g of o-(5-acetyl-6-methyl)-phenylenediamine were boiled for 40 minutes in 100 ml of 4 N HCl. The mixture was cooled and neutralized with ammonia. The neutral solution was then extracted with ethyl acetate. The organic phase was treated with active carbon and evaporated in vacuo. The residue was dissolved in acetone whereupon an equivalent of concentrated HCl was added. The precipitated hydrochloride was filtered off after cooling and the salt was recrystallized from absolute ethanol and some ether. Yield of 2-[2-(3,4,5-trimethylpyridyl)methylthio]-(5-acetyl-6-methyl)benzimidazole was 6.5 g.

This compound was then oxidized in accordance with Example 1 above, to give the corresponding sulfinyl derivative.

M.p. 190° C.

EXAMPLE 34 (METHOD C)

22.0 g of 2-mercapto-(5-acetyl-6-methyl)benzimidazole and 19.5 g of chloromethyl(4,5-dimethyl)-pyridine hydrochloride were dissolved in 200 ml of 95% ethanol. 8 g of sodium hydroxide in 20 ml of water were added, whereupon the solution was refluxed for two hours. The sodium chloride formed was filtered off and the solution was evaporated in vacuo. The residue, 2-[2-(4,5-dimethyl)pyridylmethylthio]-(5-acetyl-6-methyl)benzimidazole, was recrystallized from 70% ethanol. Yield 10.6 g.

This compound was then oxidized in accordance with Example 1 above, to give the corresponding sulfinyl derivative.

M.p. 158° C.

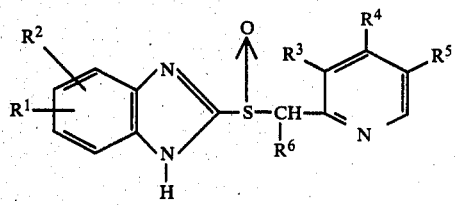

| Ex. | R¹ | R² | R⁶ | R³ | R⁴ | R⁵ | M.p. °C. |
|---|---|---|---|---|---|---|---|
| 1 | 5-COCH₃ | 6-CH₃ | H | H | CH₃ | CH₃ | 158 |
| 2 | 5-COOCH₃ | 6-CH₃ | H | H | CH₃ | CH₃ | 163 |
| 3 | 5-COOCH₃ | H | H | H | CH₃ | CH₃ | 141 |
| 4 | 5-COCH₃ | 6-CH₃ | H | CH₃ | CH₃ | H | 160 |
| 5 | 5-COOCH₃ | 6-CH₃ | H | CH₃ | CH₃ | H | 163 |
| 6 | 4-CH₃ | 6-CH₃ | H | CH₃ | H | CH₃ | 50–55 |
| 7 | 5-COCH₃ | 6-CH₃ | H | CH₃ | H | CH₃ | 171 |
| 8 | 5-COCH₃ | 6-CH₃ | H | CH₃ | CH₃ | CH₃ | 190 |
| 9 | 5-COCH₃ | 6-CH₃ | H | H | OCH₃ | H | 165 |
| 10 | 4-CH₃ | 6-CH₃ | H | H | OCH₃ | H | 122 |
| 11 | 5-COCH₃ | 6-CH₃ | H | CH₃ | OCH₃ | CH₃ | 156 |
| 12 | 5-COOCH₃ | 6-CH₃ | H | CH₃ | H | CH₃ | 144 |
| 13 | 5-COOCH₃ | 6-CH₃ | H | CH₃ | CH₃ | CH₃ | 185 |
| 14 | 5-COOCH₃ | 6-CH₃ | H | H | OCH₃ | H | 169 |
| 15 | 5-COOCH₃ | 6-CH₃ | H | H | OC₂H₅ | H | 148 |
| 16 | 5-COOCH₃ | 6-CH₃ | H | CH₃ | OCH₃ | H | 175 |
| 17 | 5-COOCH₃ | 6-CH₃ | H | CH₃ | OCH₃ | CH₃ | 155 |
| 18 | 5-COOCH₃ | 6-CH₃ | H | H | OCH₃ | CH₃ | 158 |
| 19 | 5-COOCH₃ | H | H | CH₃ | H | CH₃ | 141 |
| 20 | 5-COOCH₃ | H | H | CH₃ | OCH₃ | CH₃ | 142 |
| 21 | 5-COCH₃ | H | H | CH₃ | OCH₃ | CH₃ | 162 |
| 22 | 5-OCH₃ | H | H | H | OCH₃ | CH₃ | 178 |
| 23 | 5-OCH₃ | H | H | CH₃ | OCH₃ | CH₃ | 156 |
| 24 | 5-CH₃ | H | H | CH₃ | OCH₃ | CH₃ | 181 |
| 25 | H | H | H | CH₃ | OCH₃ | CH₃ | 165 |
| 26 | 5-Cl | H | H | CH₃ | OCH₃ | CH₃ | 185 |
| 27 | 5-CH₃ | H | H | H | OC₂H₄OCH₃ | H | 119 |
| 28 | 5-COOC₂H₅ | H | H | CH₃ | OCH₃ | CH₃ | 150–5 |
| 29 | 5-COOCH₃ | H | CH₃ | CH₃ | H | CH₃ | 130 |
| 30 | 5-CH₃ | H | H | CH₃ | CH₃ | H | 152 |

Biological effect

The compounds of the invention possess worthwhile therapeutic properties as gastric acid secretion inhibitors as demonstrated by the following tests. To determine the gastric acid secretion inhibitory properties, experiments have been performed on conscious dogs provided with gastric fistulas of conventional type and duodenal fistulas, the latter ones used for direct intraduodenal administration of the test compounds. After 18 hours starvation and deprivation of water the dogs were given a subcutaneous infusion of pentagastrin (1–4 nmol/kg, h) lasting for 6–7 hours. Gastric juice was collected in consecutive 30 minutes samples. An aliquot of each sample was titrated with 0.1 N NaOH to pH 7.0 for titrable acid concentration using an automatic titrator and pH-meter (Radiometer, Copenhagen, Denmark). Acid output was calculated as mmol $H^+$/60 minutes. The percent inhibition compared to control experiments was calculated for each compound and the peak inhibitory effect is given in Table 2 below. The test compounds, suspended in 0.5% Methocel® (methyl cellulose), were given intraduodenally in doses from 4–20 μmol/kg when the secretory response to pentagastrin has reached a steady level.

In the test prior known compounds were compared with the compounds of the present invention as will be evident from the Table 2 below.

The following gastric acid inhibiting effect data were obtained for a number of compounds tested according to the method described.

TABLE 2

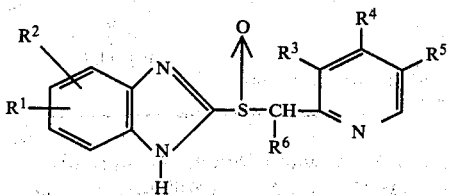

| Ex. | R¹ | R² | R⁶ | R³ | R⁴ | R⁵ | Dose μmol/kg | Effect % inhibition |
|---|---|---|---|---|---|---|---|---|
| 1 | 5-COCH₃ | 6-CH₃ | H | H | CH₃ | CH₃ | 2 | 90 |
| 4 | 5-COCH₃ | 6-CH₃ | H | CH₃ | CH₃ | H | 1 | 60 |
| 7 | 5-COCH₃ | 6-CH₃ | H | CH₃ | H | CH₃ | 2 | 100 |
| 8 | 5-COCH₃ | 6-CH₃ | H | CH₃ | CH₃ | CH₃ | 4 | 100 |
| 9 | 5-COCH₃ | 6-CH₃ | H | H | OCH₃ | H | 2 | 95 |

TABLE 2-continued

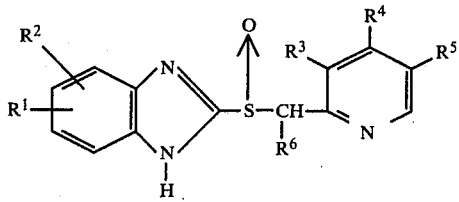

| Ex. | R¹ | R² | R⁶ | R³ | R⁴ | R⁵ | Dose μmol/kg | Effect % inhibition |
|---|---|---|---|---|---|---|---|---|
| 11 | 5-COCH₃ | 6-CH₃ | H | CH₃ | OCH₃ | CH₃ | 0.5 | 70 |
| x | 5-COCH₃ | 6-CH₃ | H | H | CH₃ | H | 20 | 30 |
| x | 5-COCH₃ | 6-CH₃ | H | H | H | CH₃ | 8 | 80 |
| 2 | 5-COOCH₃ | 6-CH₃ | H | H | CH₃ | CH₃ | 2 | 60 |
| 5 | 5-COOCH₃ | 6-CH₃ | H | CH₃ | CH₃ | H | 2 | 90 |
| 12 | 5-COOCH₃ | 6-CH₃ | H | CH₃ | H | CH₃ | 2 | 70 |
| 13 | 5-COOCH₃ | 6-CH₃ | H | CH₃ | CH₃ | CH₃ | 4 | 80 |
| 14 | 5-COOCH₃ | 6-CH₃ | H | H | OCH₃ | H | 2 | 100 |
| 15 | 5-COOCH₃ | 6-CH₃ | H | H | OC₂H₅ | H | 4 | 75 |
| 16 | 5-COOCH₃ | 6-CH₃ | H | CH₃ | OCH₃ | H | 0.5 | 65 |
| 17 | 5-COOCH₃ | 6-CH₃ | H | CH₃ | OCH₃ | CH₃ | 0.5 | 90 |
| 18 | 5-COOCH₃ | 6-CH₃ | H | H | OCH₃ | CH₃ | | |
| x | 5-COOCH₃ | 6-CH₃ | H | H | H | CH₃ | 4 | 50 |
| x | 5-COOCH₃ | 6-CH₃ | H | Br | H | H | 4 | 0 |
| 6 | 4-CH₃ | 6-CH₃ | H | CH₃ | H | CH₃ | 4 | 40 |
| 10 | 4-CH₃ | 6-CH₃ | H | H | OCH₃ | H | 2 | 40 |
| x | 4-CH₃ | 6-CH₃ | H | H | H | H | 4 | 30 |
| x | 4-CH₃ | 6-CH₃ | H | H | H | CH₃ | 12 | 50 |
| 3 | 5-COOCH₃ | H | H | H | CH₃ | CH₃ | 4 | 100 |
| 19 | 5-COOCH₃ | H | H | CH₃ | H | CH₃ | 2 | 60 |
| 20 | 5-COOCH₃ | H | H | CH₃ | OCH₃ | CH₃ | 0.5 | 65 |
| x | 5-COOCH₃ | H | H | H | H | CH₃ | 20 | 90 |
| x | 5-COOCH₃ | H | H | H | H | H | 20 | 50 |
| 21 | 5-COCH₃ | H | H | CH₃ | OCH₃ | CH₃ | 0.5 | 60 |
| x | 5-COCH₃ | H | H | H | H | C₂H₅ | 20 | 40 |
| 22 | 5-OCH₃ | H | H | H | OCH₃ | CH₃ | | |
| 23 | 5-OCH₃ | H | H | CH₃ | OCH₃ | CH₃ | 0.5 | 65 |
| x | 5-OCH₃ | H | H | H | CH₃ | H | 20 | 10 |
| 24 | 5-CH₃ | H | H | CH₃ | OCH₃ | CH₃ | 0.5 | 50 |
| x | 5-CH₃ | H | H | H | H | CH₃ | 4 | 50 |
| 25 | H | H | H | CH₃ | OCH₃ | CH₃ | 0.5 | 60 |
| x | H | H | H | H | H | H | 4 | 50 |
| 28 | 5-COOC₂H₅ | H | H | CH₃ | OCH₃ | CH₃ | 0.5 | 50 |
| 26 | 5-Cl | H | H | CH₃ | OCH₃ | CH₃ | 0.5 | 25 |
| 27 | 5-CH₃ | H | H | H | OC₂H₄OCH₃ | H | 0.5 | 30 |
| 29 | 5-COOCH₃ | H | CH₃ | CH₃ | H | CH₃ | 0.5 | 40 | x denotes a previously known compound

EXAMPLE 35

A syrup containing 2% (weight per volume) of active substance was prepared from the following ingredients:

| | |
|---|---|
| 2-[2-(4,5-dimethyl)pyridylmethylsulfinyl]-(5-acetyl-6-methyl)benzimidazole . HCl | 2.0 g |
| Saccharin | 0.6 g |
| Sugar | 30.0 g |
| Glycerin | 5.0 g |
| Flavouring agent | 0.1 g |
| Ethanol 96% | 10.0 ml |
| Distilled water (sufficient to obtain a final volume of 100 ml) | |

Sugar, saccharin and the acid addition salt were dissolved in 60 g of warm water. After cooling, glycerin and a solution of flavouring agents dissolved in ethanol were added. Water was added to the mixture to obtain a final volume of 100 ml.

The above given active substance may be replaced with other pharmaceutically acceptable acid addition salts.

EXAMPLE 36

2-[2-(3,4-dimethyl)pyridylmethylsulfinyl]-(5-acetyl-6-methyl)benzimidazole.HCl (250 g) was mixed with lactose (175.8 g), potato starch (169.7 g) and colloidal silicic acid (32 g). The mixture was moistened with 10% solution of gelatin and was ground through a 12-mesh sieve. After drying, potato starch (160 g), talc (50 g) and magnesium stearate (5 g) were added and the mixture thus obtained was pressed into tablets (10.000), with each tablet containing 25 mg of active substance. Tablets can be prepared that contain any desired amount of the active ingredient.

EXAMPLE 37

Granules were prepared from 2-[2-(3,5-dimethyl)-pyridylmethylsulfinyl]-(5-acetyl-6-methyl)benzimidazole-p-hydroxybenzoate (250 g), lactose (175.9 g) and an alcoholic solution of polyvinylpyrrolidone (25 g). After drying, the granules were mixed with talc (25 g), potato starch (40 g), and magnesium stearate (2.50 g) and were pressed into 10.000 tablets. These tablets are first coated with a 10% alcoholic solution of shellac and thereupon with an aqueous solution containing saccharose (45%), gum arabic (5%), gelatin (4%), and dyestuff (0.2%). Talc and powdered sugar were used for powdering after the first five coatings. The coating was then covered with a 66% sugar syrup and polished with a solution of 10% carnauba wax in carbon tetrachloride.

EXAMPLE 38

2-[2-(3,5-dimethyl)pyridylmethylsulfinyl]-(5-acetyl-6-methyl)benzimidazole hydrochloride (1 g), sodium chloride (0.6 g) and ascorbic acid (0.1 g) were dissolved in sufficient amount of distilled water to give 100 ml of solution. This solution, which contains 10 mg of active substance for each ml, was used in filling ampoules, which were sterilized by heating at 120° C. for 20 minutes.

We claim:
1. A compound of formula III

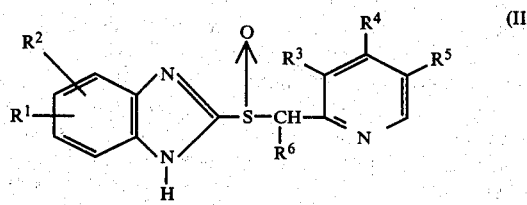

or a pharmaceutically acceptable salt thereof in which $R^1$ and $R^2$ are the same or different and are selected from the group consisting of hydrogen, alkyl having from 1–7 carbon atoms, halogen, carbomethoxy, carboethoxy, alkoxy having up to 5 carbon atoms, and alkanoyl having up to 4 carbon atoms in any position, $R^6$ is selected from the group consisting of hydrogen, methyl and ethyl, $R^3$ and $R^5$ are the same or different and are each selected from the group consisting of hydrogen, methyl, methoxy, ethoxy, methoxyethoxy and ethoxyethoxy, and $R^4$ is hydrogen or methyl whereby $R^3$, $R^4$ and $R^5$ are not all hydrogen, and whereby when two of $R^3$, $R^4$ and $R^5$ are hydrogen, the third of $R^3$, $R^4$ and $R^5$ is not methyl.

2. A compound selected from the group consisting of
2-[2-(3,4-dimethyl)-pyridylmethylsulfinyl]-(5-acetyl-6-methyl)-benzimidazole,
2-[2-(3,5-dimethyl)-pyridylmethylsulfinyl]-(4,6-dimethyl)-benzimidazole,
2-[2-(4,5-dimethyl)-pyridylmethylsulfinyl]-(5-carbomethoxy)-benzimidazole,
2-[2-(4,5-dimethyl)-pyridylmethylsulfinyl]-(5-acetyl-6-methyl)-benzimidazole,
2-[2-(4,5-dimethyl)-pyridylmethylsulfinyl]-(5-carbomethoxy-6-methyl)-benzimidazole,
2-[2-(3,4-dimethyl)-pyridylmethylsulfinyl]-(5-carbomethoxy-6-methyl)-benzimidazole,
2-[2-(3,5-dimethyl)-pyridylmethylsulfinyl]-(5-acetyl-6-methyl)-benzimidazole,
2-[2-(3,4,5-trimethyl)-pyridylmethylsulfinyl]-(5-acetyl-6-methyl)-benzimidazole,
2-[2-(3,5-dimethyl)-pyridylmethylsulfinyl]-(5-carbomethoxy-6-methyl)-benzimidazole,
2-[2-(3,4,5-trimethyl)-pyridylmethylsulfinyl]-(5-carbomethoxy-6-methyl)-benzimidazole,
2-[2-(3,5-dimethyl)-pyridylmethylsulfinyl]-(5-carbomethoxy)-benzimidazole.

3. A pharmaceutical preparation for inhibiting gastric acid secretion which contains as an active agent a compound of the formula III

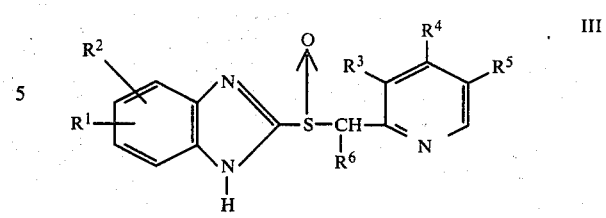

or a pharmaceutically acceptable salt thereof in a therapeutically effective amount in which $R^1$ and $R^2$ are the same or different and are selected from the group consisting of hydrogen, alkyl having from 1–7 carbon atoms, halogen, carbomethoxy, carboethoxy, alkoxy having up to 5 carbon atoms, and alkanoyl having up to 4 carbon atoms in any position, $R^6$ is selected from the group consisting of hydrogen, methyl and ethyl, $R^3$ and $R^5$ are the same or different and are each selected from the group consisting of hydrogen, methyl, methoxy, ethoxy, methoxyethoxy and ethoxyethoxy, and $R^4$ is hydrogen or methyl, whereby $R^3$, $R^4$ and $R^5$ are not all hydrogen, and whereby when two of $R^3$, $R^4$ and $R^5$ are hydrogen, the third of $R^3$, $R^4$ and $R^5$ is not methyl, said compound being associated with a pharmaceutically acceptable carrier.

4. A pharmaceutical preparation according to claim 3, in a form suitable for administration by injection wherein the compound comprises about 0.5% to about 20% by weight of the preparation.

5. A pharmaceutical preparation according to claim 3, for parenteral application which comprises an aqueous solution of a water soluble salt of said active ingredient in an amount of about 0.5 to 10% by weight of the preparation.

6. A pharmaceutical preparation according to claim 3, in a form suitable for oral administration wherein the active ingredient comprises about 2% to about 50% by weight of the preparation.

7. A pharmaceutical preparation according to claim 3, in dosage unit form suitable for oral administration wherein the dosage of active ingredient is in the range to 100 to 400 milligrams.

8. A pharmaceutical preparation according to claim 3, in dosage unit form suitable for intravenous administration wherein the dosage of active ingredient is in the range 5 to 20 milligrams.

9. A pharmaceutical preparation according to claim 3, wherein the active ingredient is selected from the group consisting of
2-[2-(3,4-dimethyl)-pyridylmethylsulfinyl]-(5-acetyl-6-methyl)-benzimidazole,
2-[2-(3,5-dimethyl)-pyridylmethylsulfinyl]-(4,6-dimethyl)-benzimidazole,
2-[2-(4,5-dimethyl)-pyridylmethylsulfinyl]-(5-carbomethoxy)-benzimidazole,
2-[2-(4,5-dimethyl)-pyridylmethylsulfinyl]-(5-acetyl-6-methyl)-benzimidazole,
2-[2-(4,5-dimethyl)-pyridylmethylsulfinyl]-(5-carbomethoxy-6-methyl)-benzimidazole,
2-[2-(3,4-dimethyl)-pyridylmethylsulfinyl]-(5-carbomethoxy-6-methyl)-benzimidazole,
2-[2-(3,5-dimethyl)-pyridylmethylsulfinyl]-(5-acetyl-6-methyl)-benzimidazole,
2-[2-(3,4,5-trimethyl)-pyridylmethylsulfinyl]-(5-acetyl-6-methyl)-benzimidazole, 2-[2-(3,5-dimethyl)-pyridylmethylsulfinyl]-(5-carbomethoxy-6-methyl)-benzimidazole, 2-[2-(3,4,5-trimethyl)-pyridylmethylsulfinyl]-(5-carbomethoxy-6-methyl)-benzimidazole, 2-[2-(3,5-dimethyl)-pyridylmethylsulfinyl]-(5-carbomethoxy)-benzimidazole.

10. A pharmaceutical preparation according to claim 3, wherein the active ingredient is 2-[2-(3,5-dimethyl)-pyridylmethylsulfinyl]-(4,6-dimethyl)-benzimidazole or a pharmaceutically acceptable, non-toxic addition salt thereof in a therapeutically effective amount.

11. A pharmaceutical preparation according to claim 3, wherein the active ingredient is 2-[2-(3,5-dimethyl)-pyridylmethylsulfinyl]-(5-acetyl-6-methyl)-benzimidazole or a pharmaceutically acceptable, non-toxic addition salt thereof in a therapeutically effective amount.

12. A pharmaceutical preparation according to claim 3, wherein the active ingredient is 2-[2-(3,4-dimethyl)-pyridylmethylsulfinyl]-(5-acetyl-6-methyl)-benzimidazole or a pharmaceutically acceptable non-toxic addition salt thereof in a therapeutically effective amount.

13. A pharmaceutical preparation according to claim 3, wherein the active ingredient is 2-[2-(3,4-dimethyl)-pyridylmethylsulfinyl]-(5-carbomethoxy-6-methyl)-benzimidazole or a pharmaceutically acceptable non-toxic acid addition salt thereof in a therapeutically effective amount.

14. A pharmaceutical preparation according to claim 3, wherein the active ingredient is 2-[2-(3,5-dimethyl)-pyridylmethylsulfinyl]-(5-carbomethoxy-6-methyl)-benzimidazole or a pharmaceutically acceptable, non-toxic acid addition salt thereof in a therapeutically effective amount.

15. A pharmaceutical preparation according to claim 3, wherein the active ingredient is 2-[2-(4,5-dimethyl)-pyridylmethylsulfinyl]-(5-acetyl-6-methyl)-benzimidazole or a pharmaceutically acceptable, non-toxic acid addition salt thereof in a therapeutically effective amount.

16. A pharmaceutical preparation according to claim 3, wherein the active ingredient is 2-[2-(4,5-dimethyl)-pyridylmethylsulfinyl]-(5-carbomethoxy-6-methyl)-benzimidazole or a pharmaceutically acceptable, non-toxic acid addition salt thereof in a therapeutically effective amount.

17. A pharmaceutical preparation according to claim 3, wherein the active ingredient is 2-[2-(4,5-dimethyl)-pyridylmethylsulfinyl]-(5-carbomethoxy)-benzimidazole or a pharmaceutically acceptable, non-toxic acid addition salt thereof in a therapeutically effective amount.

18. A pharmaceutical preparation according to claim 3, wherein the active ingredient is 2-[2-(3,4,5-trimethyl)-pyridylmethylsulfinyl]-(5-acetyl-6-methyl)-benzimidazole or a pharmaceutically acceptable, non-toxic acid addition salt thereof in a therapeutically effective amount.

19. A pharmaceutical preparation according to claim 3, wherein the active ingredient is 2-[2-(3,4,5-trimethyl)-pyridylmethylsulfinyl]-(5-carbomethoxy-6-methyl)-benzimidazole or a pharmaceutically acceptable, non-toxic acid addition salt thereof in a therapeutically effective amount.

20. A pharmaceutical preparation according to claim 3, wherein the active ingredient is 2-[2-(3,5-dimethyl)-pyridylmethylsulfinyl-(5-carbomethoxy)-benzimidazole or a pharmaceutically acceptable, non-toxic acid addition salt thereof in a therapeutically effective amount.

21. A method of inhibiting gastric acid secretion by administering to mammals, including man, suffering from gastric acid secretion disturbances a compound of the formula III

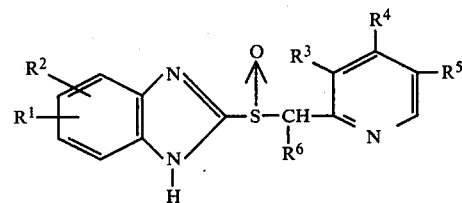

or a pharmaceutically acceptable salt thereof in a therapeutically effective amount in which $R^1$ and $R^2$ are the same or different and are selected from the group consisting of hydrogen, alkyl having from 1–7 carbon atoms, halogen, carbomethoxy, carboethoxy, alkoxy having up to 5 carbon atoms, and alkanoyl having up to 4 carbon atoms in any position, $R^6$ is selected from the group consisting of hydrogen, methyl and ethyl, $R^3$ and $R^5$ are the same or different and are each selected from the group consisting of hydrogen, methyl, methoxy, ethoxy, methoxyethoxy and ethoxyethoxy, and $R^4$ is hydrogen or methyl whereby $R^3$, $R^4$ and $R^5$ are not all hydrogen, and whereby when two of $R^3$, $R^4$ and $R^5$ are hydrogen, the third of $R^3$, $R^4$ and $R^5$ is not methyl.

22. A method according to claim 21, wherein a compound of formula III selected from the group consisting of 2-[2-(3,4-dimethyl)-pyridylmethylsulfinyl]-(5-acetyl-6-methyl)-benzimidazole, 2-[2-(3,5-dimethyl)-pyridylmethylsulfinyl]-(4,6-dimethyl)-benzimidazole, 2-[2-(4,5-dimethyl)-pyridylmethylsulfinyl]-(5-carbomethoxy)-benzimidazole, 2-[2-(4,5-dimethyl)-pyridylmethylsulfinyl]-(5-acetyl-6-methyl)benzimidazole, 2-[2-(4,5-dimethyl)-pyridylmethylsulfinyl]-(5-carbomethoxy-6-methyl)-benzimidazole, 2-[2-(3,4-dimethyl)-pyridylmethylsulfinyl]-(5-carbomethoxy-6-methyl)-benzimidazole, 2-[2-(3,5-dimethyl)-pyridylmethylsulfinyl]-(5-acetyl-6-methyl)-benzimidazole, 2-[2-(3,4,5-trimethyl)-pyridylmethylsulfinyl]-(5-acetyl-6-methyl)-benzimidazole, 2-[2-(3,5-dimethyl)-pyridylmethylsulfinyl]-(5-carbomethoxy-6-methyl)-benzimidazole, 2-[2-(3,4,5-trimethyl)-pyridylmethylsulfinyl]-(5-carbomethoxy-6-methyl)-benzimidazole, 2-[2-(3,5-dimethyl)-pyridylmethylsulfinyl]-(5-carbomethoxy)-benzimidazole.

23. An intermediate of the formula

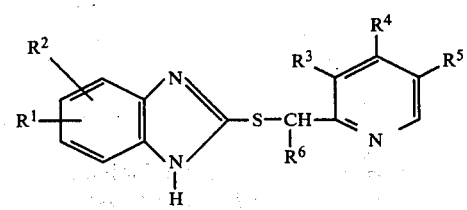

wherein $R^1$ and $R^2$ are the same or different and are selected from the group consisting of hydrogen, alkyl having from 1-7 carbon atoms, halogen, carbomethoxy, carboethoxy, alkoxy having up to 5 carbon atoms, and alkanoyl having up to 4 carbon atoms, $R^6$ is selected from the group consisting of hydrogen, methyl and ethyl, and $R^3$ and $R^5$ are the same or different and are selected from the group consisting of hydrogen, methyl, methoxy, ethoxy, methoxyethoxy, and ethoxyethoxy, and $R^4$ is hydrogen or methyl, whereby $R^3$, $R^4$ and $R^5$ are not all hydrogen and whereby when two of $R^3$, $R^4$ and $R^5$ are hydrogen, the third of $R^3$, $R^4$ and $R^5$ is not methyl.

* * * * *

UNITED STATES PATENT AND TRADEMARK OFFICE
CERTIFICATE OF CORRECTION

PATENT NO. : 4,337,257

DATED : June 29, 1982

INVENTOR(S) : Junggren et al.

It is certified that error appears in the above—identified patent and that said Letters Patent is hereby corrected as shown below:

Col. 4, line 1, "(VII)" should read --(VI)--;
Col. 5, line 9, "halosucinimide" should read --halosuccinimide--
Col. 5, line 21, "or or" should read --or--;
Col. 7, line 24, insert a comma after "boxes";
      line 31, "The following" should start a new paragraph;
Col. 14, line 44, before "100" delete "to";
Col. 15, line 68, "pyridylmethylsulfinyl-" should read --pyridymethylsulfinyl]- --
Col. 16, line 32, "a" should read --said--;
      line 33, after "III" insert --is--.

Signed and Sealed this

Thirty-first Day of August 1982

[SEAL]

Attest:

GERALD J. MOSSINGHOFF

Attesting Officer     Commissioner of Patents and Trademarks